US00PP13104P2

(12) United States Plant Patent
Olesen et al.

(10) Patent No.: US PP13,104 P2
(45) Date of Patent: Oct. 22, 2002

(54) MINIATURE ROSE PLANT NAMED 'POULSIV'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 23 days.

(21) Appl. No.: 09/655,260

(22) Filed: Sep. 5, 2000

(51) Int. Cl.[7] ..... A01H 5/00

(52) U.S. Cl. ..... Plt./118

(58) Field of Search ..... Plt./118, 125, 145

(56) References Cited

PUBLICATIONS

UPOV–ROM, 2001/03, Plant Variety Database, GTI Jouve Retrieval Software, 2 citations for 'POULsiv'.*

Cooper, "Biotechnology and the Law", Section 8.05, (1998 Clark Boardman, Callaghan), pp. 8–15 to 8–16.*

Community Plant Variety Office. "Certificate on the Grant of Community Plant Variety Rights" Jun. 19, 2000. 6 pages. EU.

* cited by examiner

*Primary Examiner*—Howard J. Locker

(57) ABSTRACT

A new miniature rose plant which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and an unnamed seedling. The two parents were crossed and the resulting seeds were planted in a controlled environment. The new variety is named 'POULsiv'.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

The combination of qualities of this variety represents significant improvement over previously available commercial cultivars of this type and distinguishes 'POULsiv' from all other varieties of which we are aware. As part of their rose development program, L. Pernille Olesen and Mogens N. Olesen germinated the seeds from the aforementioned hybridization and conducted evaluations on the resulting seedlings in a controlled environment in Fredensborg, Denmark.

'POULsiv' was selected by the inventors as a single plant from the progeny of the hybridization in Fredensborg, Denmark.

Asexual reproduction of 'POULsiv' by cuttings and traditional budding onto *Rosa multiflora* understock was first done by L. Pernille and Mogens N. Olesen in their nursery in Fredensborg, Denmark on Aug. 2, 1996. This initial and other subsequent propagations conducted in controlled environments have demonstrated that the characteristics of 'POULsiv' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULsiv'. Specifically illustrated in SHEET 1:

1. Stem showing the attachment of leaves, bud, and peduncle;
2. Flower bud, partially opened bud, and open bloom;
3. Flower petals, detached;
4. Sepals, receptacle, and pedicel;
5. Flowering stem as well as a bare stem exhibiting thorns;
6. Leaves.

DETAILED DESCRIPTION OF THE VARIETY

The following is a description of 'POULsiv', as observed in its growth in Half Moon Bay, Calif. Color references are made using The Royal Horticultural Society (London, England) Colour Chart, 1995, except where common terms of color are used.

For a comparison, several physical characteristics of the rose variety 'POULmoon', a rose variety from the same inventors described and illustrated in U.S. Plant patent application Ser. No. 09/136,896 dated Aug. 18, 1998 are compared to 'POULsiv' in Chart 1.

CHART 1

| | 'POULsiv' | 'POULmoon' |
|---|---|---|
| Petal: upper surface | Yellow Group 5C. | Yellow-Green Group 4C & Yellow-Green Group 6D. |

CHART 1-continued

| | 'POULsiv' | 'POULmoon' |
|---|---|---|
| Petal: lower surface | Yellow Group 5C. | Yellow-Green 4C & Yellow-Green 6D. |
| Petalage | Very Double: 50–55. | Double: 35–40 |

PARENTS

Classification:
*Botanical.*—*Rosa hybrida.*
*Commercial.*—Miniature.

FLOWER AND FLOWER BUD

Blooming habit: Recurrent.
Flower bud:
*Size.*—Upon opening, 23 mm–25 mm in length from base of receptacle to end of bud.
*Bud form.*—Short, globular.
*Bud color.*—As sepals unfold, Yellow-Green Group 154A Yellow Group 12 A–B at ¼ opening.
*Sepals.*—Yellow-Green Group 144A. Moderate to weak foliaceous appendages on three of the five sepals. Surfaces of sepals slightly pubescent. Stipitate glands are present on edges of the sepals.
*Receptacle.*—Surface: Smooth, somewhat glossy. Shape: Cup-shaped. Size: 5 mm (h)×9 mm (w). Color: Yellow-Green Group 144A.
*Peduncle.*—Surface: Moderately populated with stipitate glands. Length: 25 to 30 mm average length. Color: Green Group 143B. Strength: Upright.
*Borne.*—Singly.
Flower bloom:
*Fragrance.*—Light.
*Duration.*—As a pot plant, flowers last from 6 to 7 days. As a cut flower 3 to 6 days. Petals fall cleanly away from plant.
*Size.*—Medium for a 12.5 cm pot rose. Average flower diameter is 40 mm when open.
*Form.*—Shape of flower when viewed from the side: Upon opening, upper part: Flattened convex. Upon opening, lower part: Flattened convex. Open flower, upper part: Flat. Open flower, lower part: Flattened convex.
*Petalage.*—Average range: 50 to 55 petals under normal conditions with 3 to 5 petaloids.
Color:
*Upon opening, petals.*—Outermost petals: Upper Surface: Yellow Group 8B. Reverse Side: Yellow Group 8B with intonations of Yellow Group 8D. Innermost petals: Upper Surface: Yellow Group 8 B–C. Reverse Side: Yellow Group 8 B–C.
*Upon opening, basal petal spots.*—No distinctive coloration at petal base observed.
*After opening, petals.*—Outermost petals: Upper Surface: Yellow Group 5C. Reverse Side: Yellow Group 5C. Innermost petals: Upper Surface: Yellow Group 5C. Reverse Side: Yellow Group 5C.
*After opening, basal petal spots.*—No distinctive coloration at petal base observed.
General tonality: On open flower Yellow Group 8 A–B. No change in the general tonality at the end of the 6th day. Afterwards, general tonality is Yellow Group 5C.
Petals:
*Petal reflex.*—Strong.
*Petal edge.*—Uniform.
*Shape.*—Round.
*Petaloids.*—3 to 5 petaloids.
*Texture.*—Average thickness.
*Arrangement.*—Imbricated.
Reproductive organs:
*Pollen.*—Color: Greyed-Orange Group 167A. Abundance: Limited.
*Anthers.*—Size: Small. Color: Brown Group 200B. Abundance: Average.
*Filaments.*—Color: Yellow Group 3A.
*Stigmas.*—Slightly inferior in position relative to anthers. Color: Yellow Green Group 154C.
*Styles.*—Color: Yellow Green Group 145D.
*Seed formation.*—Hips not observed.

PLANT

Plant growth: Vigorous, compact. When grown in a 12.5 cm pot plant, as is typical in the production of the variety, the average height of the plant is 24 to 30 cm and the average width is 26 to 30 cm.
Stems:
*Color.*—Young wood: Yellow Green Group 144A. Older wood: Yellow Green Group 144A.
*Prickles.*—Incidence: Few. Size: Average length: 4 mm–5 mm. Color: Yellow Green Group 145B with intonations of Greyed-Red Group 181A. Shape: Linear.
*Surface.*—Young wood: Smooth. Older wood: Smooth.
Plant foliage: Normal number of leaflets on normal leaves in middle of the stem: 5 leaflets.
*Leaf size.*—50 mm (l)×30 mm (w).
*Abundance.*—Very abundant.
*Color.*—Upper Leaf Surface: Green Group 139A. Lower Leaf Surface: Green Group 138B. Juvenile foliage: Yellow-Green Group 144B–C. Anthocyanin intonation: Location: When present, barely visible along edges of leaflet. Color: Greyed-Purple Group 185B.
Plant leaves and leaflets:
*Stipules.*—Size: 5 mm–7 mm. Color: Green Group 139A at the base, Yellow Green Group 144C at tips. Presence of stipitate glands: Present on edges of tips.
*Petiole.*—Length: 15 mm–20 mm. Color: Yellow-Green Group 144A. Underneath: Yellow Green Group 144A. Margins: Green Group 139A.
*Rachis.*—Color: Yellow-Green Group 144A. Underneath: Yellow Green Group 144A. Margins: Green Group 139A.
*Leaflet.*—Edge: Serrated. Shape: Ovate. Texture: Thick and somewhat glossy.
Disease resistance: Average resistance to mildew, black spot, and Botrytis under normal growing conditions in Half Moon Bay.
Cold hardiness: 'POULsiv' has been found to be resistant to damage from cold, heat and drought damage in USDA Zone 7.
We claim:
1. A new and distinct variety of rose plant of the miniature class, substantially as herein illustrated and described as a distinct and novel rose variety due to its abundant, yellow flowers, vigorous and compact growth, year round flowering under glasshouse conditions, suitability for production from softwood cuttings in pots, and durable flowers and foliage which make the variety suitable for distribution in the floral industry.

* * * * *

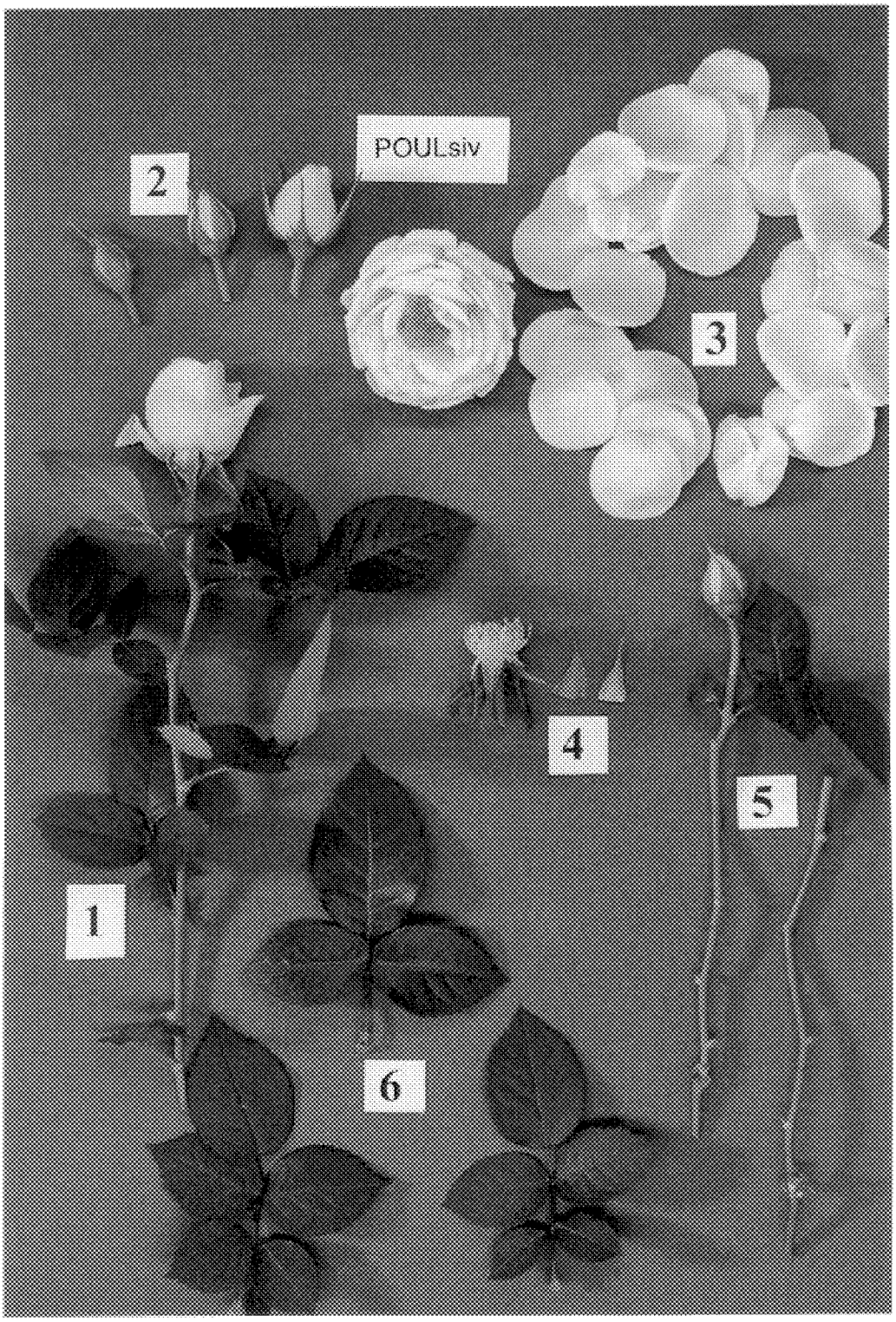
POULsiv
2
3
4
5
1
6